(12) United States Patent
Blum

(10) Patent No.: US 6,569,635 B1
(45) Date of Patent: May 27, 2003

(54) GROWTH STATE-SPECIFIC IMMUNOFLUORESCENT PROBES FOR DETERMINING PHYSIOLOGICAL STATE AND METHOD OF USE

(75) Inventor: Paul Blum, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/313,277

(22) Filed: May 18, 1999

Related U.S. Application Data

(60) Provisional application No. 60/085,897, filed on May 18, 1998.

(51) Int. Cl.[7] ............. G01N 33/53; G01N 33/554; G01N 33/569; C12Q 1/10; C12N 15/09
(52) U.S. Cl. ............. 435/7.32; 435/7.1; 435/7.37; 435/7.93; 435/7.94; 435/7.95; 435/38; 435/69.3; 435/235.1; 435/252.33; 435/252.8; 436/512; 930/81; 930/82; 930/208; 935/81
(58) Field of Search ............. 435/7.1, 7.37, 435/7.93, 7.94, 7.95, 38, 69.3, 235.1, 252.33, 252.8, 802, 803, 807; 436/512; 930/81, 82, 208; 935/81

(56) References Cited

U.S. PATENT DOCUMENTS 4,690,890 A * 9/1987 Loor et al. ............. 435/7

OTHER PUBLICATIONS

Desmonts et al. 1990. Applied and Environ. Microbio. 56(5): 1448–1452.*
Del Mar Lleo, M., et al. (1998). "Nonculturable *Enterococcus faecalis* Cells are Metabolically Active and Capable of Resuming Active Growth." *System. Appl. Microbiol.* 21:333–339.
Rockabrand, D., et al., (1999). "Bacterial Growth State Distinguished by Single–Cell Protein Profiling: Does Chlorination Kill Coliforms in Municipal Effluent?" *Applied and Env. Microbiol.* 65:4181–4188.
Almiron et al. 1992. Genes & Devel. 6: 2646–2654.*
Krska et al. 1993. J. of Bacterio. 175(20): 6433–6440.*
Nilsson et al. 1992. J. of Bacterio. 174(3): 921–929.*
O'Reilly et al. 1997. J. of Bacterio. 179(2): 522–529.*
Rockabrand et al. 1995. Mol. Gen. Genet 249:498–506.*
Rockabrand et al. 1998. J. of Bacterio. 180(4): 846–854.*

* cited by examiner

*Primary Examiner*—Lynette R. F. Smith
*Assistant Examiner*—Ja Na Hines
(74) *Attorney, Agent, or Firm*—Jondle & Associates PC

(57) ABSTRACT

A novel method for examining bacterial growth state is carried out by measuring the levels of conserved cytosolic proteins specific for alternative growth states, using bacterial specific antibody fluorochrome-coupled probe. Utilizing the method of the invention, the cellular growth state of individual bacteria can be determined by measuring the abundance of growth state-specific protein homologs. For example, through use of the protein profiling method of the invention, bacterial VNC state can be distinguished by differentiating growing (exponential phase) from nongrowing or dormant (stationary phase) cells.

15 Claims, 6 Drawing Sheets

GROWTH STATE-SPECIFIC IMMUNOFLUORESCENT PROBES FOR DETERMINING PHYSIOLOGICAL STATE AND METHOD OF USE

This application is related to U.S. provisional patent application Serial No. 60/085,897 filed May 18, 1998, incorporated herein by reference.

BACKGROUND OF INVENTION

The present invention is directed to growth-state specific probes and to a method for distinguishing physiological status of bacterial cells through use of such probes, more particularly the growth state of individual bacterial cells. The present invention is especially useful for distinguishing growing from dormant or viable but nonculturable bacterial cells.

The publications and other materials used herein to illuminate the background of the invention, and in particular cases, to provide additional details respecting the practice, are incorporated by reference, and for convenience are referenced in the following text by author and date and are listed alphabetically by author in the appended bibliography.

Civilization has long recognized the relationship between fecal contamination and the outbreak of communicable disease. Two categories of bacteria routinely tested as indicative of fecal contamination are *Escherichia coli* and total coliforms. The Environmental Protection Agency (EPA) requires monitoring of coliform content in wastewater effluent prior to its release into recreational waters. Most U.S. communities are located in close proximity to such waterways. The EPA requires that discharged municipal effluent contain no more than 4,000 fecal coliforms per liter (Eaton et al., 1995). To meet these requirements, fecal coliform content usually is adjusted by chlorination with chlorine gas or chloramines followed by residual chlorine neutralization with sulfur dioxide (Fed. Regist. 60:62562). Since wastewater comprises a diverse community of microbial taxa, standard procedures for fecal coliform enumeration rely on selective enrichment techniques using detergent additives (Eaton et al., 1995). However, studies on coliform regrowth in chlorinated drinking water indicate that such techniques significantly underestimate coliform death due to chlorine injury that induces a viable but nonculturable "VNC" state. (Camper and McFeters, 1979; McFeters et al., 1986; McFeters, 1990). Because resuscitation of injured cells can occur upon nutrient resupplement, it is well recognized that most standard procedures may underestimate the incidence of the indicator species and therefore distort water quality estimates (Dawes and Penrose, 1978; Postgate and Hunter, 1962; Xu et al., 1982).

Many factors which limit bacterial proliferation can precipitate the VNC or dormant state (Morita, 1997; Oliver, 1993). Recent data indicates that VNC forms remain potentially pathogenic. Dormancy has been characterized in great detail in *Vibrio* (Rockabrand et al., 1995; Whitesides and Oliver, 1997) and is of particular importance in estimating the occurrence of cholera, a water-borne disease (Colwell, 1996). In natural samples, the disparity between total and culturable cell counts and the diversity of 16S rRNA sequences apparent in uncultivated samples compared to culture collections, indicate that most bacteria are unculturable (Staley and Konopka, 1985). This suggests that dormancy is widespread. Despite efforts to clarify the physiological basis for this state, the relationship between dormancy and culturability has remained unclear. In contrast, much has been learned about the early stationary phase which precedes dormancy (Blum, 1997; Goodrich-Blair et al., 1996; Hengge-Aronis, 1996). Current understanding and strategies for the analysis of the VNC state are limited. Thus, there is a definite need to understand the VNC state and determine the physiological status and the relationship between dormancy and culturability and for development of new methodologies capable of detecting microorganisms in the VNC state.

Utilization of bacteria in industrial settings has become common. For example, microbial-based hazardous waste treatment processes (bioremediation) have been applied to the treatment of numerous hazardous wastes and associated liquids including: refinery and petrochemical production oily sludges and asphaltic type wastes, process waste slurries from organic chemicals production and soils contaminated with fuel oils. Bioremediation involves exploiting abilities of indigenous or augmented microorganisms to metabolize organic susbstrates. Bioremediation systems are designed to achieve optimal conditions for microbial degradation. To this end, it is desirable to prevent bacterial growth limitations. The prevention of bacterial growth limitations requires accurate assessment and monitoring of the physiology and growth state of the bacteria.

Availability of recombinant bacteria have facilitated the industrial production of various enzymes and other proteins of therapeutic value. *Escherichia coli* is the most frequently used prokaryotic expression system for the production of heterologous proteins, including recombinant antibodies. Proteins made in *E. coli* have been widely used in detection, imaging, diagnosis, and therapy. In order to increase fermenter productivity, cell density in culture in excess of 100 g dry weight/L is desirable; however, cells at higher densities are difficult to maintain and the cells are more likely to die. Therefore, careful monitoring of growth state is necessary to assure productivity.

Assessment of the progress of treatment of human and animal diseases with antimicrobial agents relies on conventional culturability measurements. Assessment based on detection of only culturable cells may overestimate success of treatment due to the presence of dormant bacteria. Thus, it is desirable to establish new methodologies capable of detecting bacterial growth state for use in a variety of applications, including: treatment of wastewater, industrial fermentations, bioremediation and treatment of bacterial disease. The present invention solves this need as illustrated herein.

SUMMARY OF THE INVENTION

Utilization of bacteria in industrial settings has become common. For example, microbial-based hazardous waste treatment processes (bioremediation) have been applied to the treatment of numerous hazardous wastes and associated liquids including: refinery and petrochemical production oily sludges and asphaltic type wastes, process waste slurries from organic chemicals production and soils contaminated with fuel oils. Bioremediation involves exploiting abilities of indigenous or augmented microorganisms to metabolize organic substrates. Bioremediation systems are designed to achieve optimal conditions for microbial degradation. To this end, it is desirable to prevent bacterial growth limitations. The prevention of bacterial growth limitations requires accurate assessment and monitoring of the physiology and growth state of the bacteria.

SUMMARY OF SEQUENCE LISTING

Figure 1:
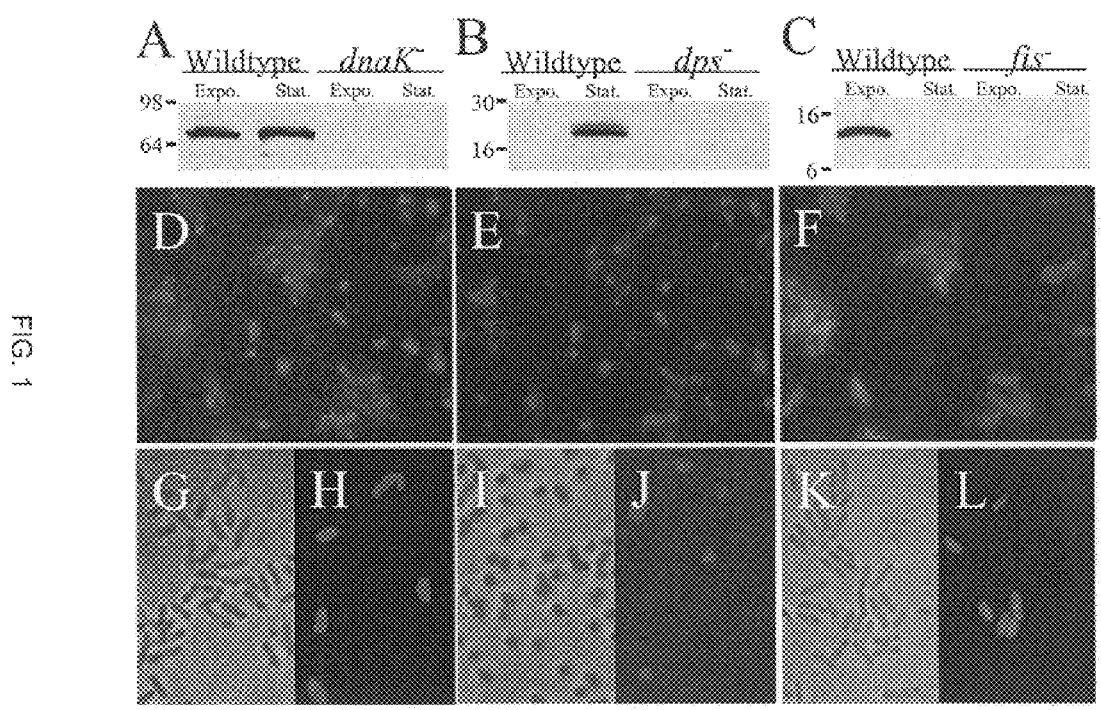
FIG. 1 Growth State and Target Protein Specificity of Antibody Probes. Western blots of various cell extracts of growing (exponential phase; Expo.) and starving (stationary phase; Stat.) wild type (lanes 1 and 2) and mutant *E. coli* (lanes 3 and 4) strains visualized by chemiluminescence (A–C). Lanes Molecular mass standards are indicated. Single exposure fluorescent micrographs of growing and starving wild type *E. coli* mixed at a 1:1 ratio probed with the three fluorochrome labeled antibody probes and visualized using fluor-specific filters; AMCA labeled anti-DnaK (D), TEXAS REDυ (a sulfonyl chloride derivative of Sulforhodamine 101) labeled anti-Dps (E), and FITC labeled anti-Fis antibodies (F). Bright field and single exposure fluorescent micrographs of wild type and mutant *E. coli* mixed at a 1:5 ratio probed with AMCA labeled anti-DnaK antibody (G, H), TEXAS RED™ labeled anti-Dps antibody (I, J) and FITC labeled anti-Fis antibody (K, L). Left panel in each set (G–L) is a phase contrast bright field image of the same field viewed by fluorescence in the right panel.

SEQ ID No: 1 is a primer from PBL500 used to amplify the fis gene.

SEQ ID No: 2 is a primer from PBL500 used to amplify the fis gene.

SEQ ID No: 3 is a 16S rRNA probe specific for Enterobacteriaceae.

DETAILED DESCRIPTION OF THE INVENTION

The present invention is directed to growth-state specific probes and to a method for distinguishing physiological status of bacterial cells through the use of such probes, more particularly the growth state of individual bacterial cells. The present invention is especially useful for distinguishing growing from dormant or viable but nonculturable bacterial cells.

The present invention is directed to antibody probes for bacterial growth state-specific proteins. Growth state-specific proteins were purified to homogeneity from recombinant bacterial strain extracts. The antibodies were raised, purified and analyzed. The specificity of the antibodies was confirmed by western blot using extracts of wild-type or mutant bacterial strains from exponentially growing and from starving cultures. These antibody probes were confirmed to be growth state-specific and target protein dependent. The antibodies were labeled and used to probe single bacterial cells. In a preferred embodiment of the invention, the growth state-specific proteins, DnaK, Dps, and Fis, were purified from recombinant *E. coli* strain extracts. Detection by use of antibodies can be performed by those means known in the art including radioactive labeling, ferritin labeling, ELISA immunoblotting, immunoprecipitation and fluorescence conjugation. For purposes of description, fluorescence conjugation is preferred; however, it is understood that other methods of detection are equally applicable.

The present invention is also directed to a method for monitoring growth state of bacteria in a sample by detecting the presence of growth state-specific proteins in the cells. In a preferred embodiment, antibodies are labeled using IgG antibody-fluorochrome conjugates (Table 1) and the fluor-labeled antibody probes are combined with the bacterial cell sample. The fluor-labeled antibodies bind to the target proteins present in the bacterial cells. A cell probed with a mixture of these labeled antibodies emits one or more color(s) depending upon which proteins are present in the cell, and thereby identifies the growth state of that particular cell. Subpopulations of the bacterial cells in the sample are distinguished by characteristics of the emission.

TABLE 1

| Antibody specificity | Fluorochrome | Color |
|---|---|---|
| DnaK | AMCA | Blue |
| Dps | TEXAS RED ™ | Red |
| Fis | FITC | Green |

In a preferred embodiment of the method of the invention, subpopulations of uncultivated bacterial samples are distinguished by detection of growth state-specific proteins present in the cells. The preferred labels are fluorescent markers and the signal to be detected is fluorescence emission; however, other conventional methods of detecting the growth state-specific proteins could be employed, such as western blot procedures and ELISA.

In a most preferred embodiment of the method of the present invention, detection of cytosolic growth state-specific proteins produced by coliforms, Dps, Fis and DnaK, is accomplished using fluorescent microscopy procedures. Because standard methods for disinfection of wastewater result in chlorine injured coliforms, the treatment and response of these cells presents a convenient model for understanding the VNC state. (Table 2). However, the present invention is not limited to chlorine injured coliforms; rather, it encompasses use of the invention for understanding the VNC state induced by any injury such as would result from the imposition of heat, pressure, irradiation or other treatments designed to remove unwanted bacteria. Determination of growth state-specific protein ratios defines the VNC state and provides a new strategy for understanding the consequences of uncoupling bacterial growth from survival. The evidence presented here demonstrates the utility of the protein profiling method of the invention for studies on the major enteric bacterial genera and possess Dps and Fis homologs or other proteins with similar growth state characteristics.

TABLE 2

Chlorine addition to wastewater effluent results in the VNC phenotype

| Chlorine addition | Growth Media | | % Injury |
|---|---|---|---|
| | m-T7 | m-Endo | |
| + | $5.30 \times 10^5$ CFU/ml | $4.92 \times 10^3$ CFU/ml | 92.8 |
| − | $4.85 \times 10^5$ CFU/ml | $5.02 \times 10^5$ CFU/ml | 0.0 |

Wastewater samples pre and post chlorination were plated on m-T7 and m-Endo agar plate in duplicate and incubated at 35 degrees C. overnight.

In accordance with the method of the present invention, protein profiling of highly conserved bacterial growth state-specific proteins, for example, Fis, Dps and DnaK, is possible. (Rockabrand, et al., in review). DnaK (HSP70), a molecular chaperone (Georgopoulos, 1992; Mayhew, 1996), plays a critical role in both exponential and stationary phase physiology (Bukau and Walker, 1989; Rockabrand, 1995; Spence et al., 1990). DnaK is a metabolically stable protein whose abundance changes only moderately in response to nutrient deprivation (Rockabrand et al., 1998) permitting its use as a control for probe access and hybridization. Dps is a 19 kDa highly conserved DNA binding protein (Almiron et al., 1992; Lomovskaya et al., 1994) which is important in stationary phase stress physiology (Almiron et al., 1992; Lomovskaya et al., 1994; Rockabrand et al., 1998). Dps abundance is inversely correlated with growth rate and it varies in cellular concentration over 100-fold between the extremes of stationary phase and rapid growth (Almiron et al., 1992; Lomovskaya et al., 1994; Notley and Ferenci, 1996; Rockabrand et al., 1998). Dps abundance was used as a positive indicator of dormancy (e.g., starvation or stationary phase). Fis is an 11 kDa DNA binding protein (Johnson et al., 1998; Coch et al., 1988) which plays a critical role coordinating rRNA synthesis with growth (Nilsson et al., 1992). Fis therefore is present in replicating cells and its abundance is directly correlated with growth rate (Ball et al., 1992; Thompson et al., 1987). Fis abundance varies over 500-fold between the extremes of rapid growth and stationary phase. Fis abundance was used as a positive indicator of growth. Thus, exponentially growing cells have high levels of Fis and undetectable levels of Dps. Cells starved for even one day exhibit an inverse pattern of expression characterized by undetectable levels of Fis and high levels of Dps. Intermediate levels of Fis and Dps are evident and occur in response to physiological transitions.

Preparation of Plasmids, Culture of Bacteria and Strain Construction.

*Escherichia coli* K-12 strains used were PBL500 (lacZ:Tn5 lacI$^{q1}$) and PBL501 (ΔdnaK52::Cm$^r$ lacZ::Tn5 lacI$^{q1}$) (Rockabrand, et al., 1995), PBL755 (Δfis::Tn10) and PBL664 (Δdps) were constructed as described herein, DH5α (ϕ80dlacZΔM15(lacZYA-argF) U169 deoR recA1 endA1 hsdR17 ($r_k^-m_k^+$) supE44 thi-1 gyrA69) was obtained from the manufacturer (Gibco-BRL). Cell densities in both growing and starving cultures were monitored spectrophotometrically at a wavelength of 600 nm. The media used were LB (Miller, 1972), m-T7 (Difco), M-Endo (BBL), Lauryl Tryptose broth (Difco), and EC broth (BBL). The medium used for the Tet$^5$ selections was prepared as described previously in Bochner, et al. (1980). Ampicillin and tetracycline were added at final concentrations of 100 μg/ml and 12 μg/ml, respectively. Tests for chlorine injury of wastewater organisms were performed by spread plating wastewater effluent dilutions with and without chlorination onto m-T7 or m-Endo agar plates in duplicate. Less than 1% variation was observed between replicate samples. Most probably numbers (MPN) values were determined as described previously in Eaton, et al. (1995). The bacteria in raw wastewater samples were allowed to exhaust endogenous nutrients by continued incubation at ambient temperatures with gentle shaking in flasks until total cell numbers were observed to undergo no further increase.

Molecular biology methods were performed as described in Blum, et al. (1992), and Rockabrand, et al. (1995). Analysis of DNA sequences was as described in Partridge, et al. (1993). The fis mutant was constructed by phage M13 mediated recombination (Blum, et al., 1989). A 2.1 kb HindIII fragment spanning fis from phage λ-529 (Kohara, et al., 1987), was ligated into the HindIII site of pACYC177 (New England Biolabs). The tet$^r$ gene from pBR322 (Gibco-BRL) was subcloned as a 1.4 kb EcoRI-StyI fragment into pUC19 (New England Biolabs) at the EcoRI-XbaI sites and then subcloned again as a 1.7 kb PvuII fragment into the HpaI site at nt 48 of fis. The region spanning the disrupted fis gene was subcloned as a 3.5 kb AgeI-NsiI fragment into the XmnI-PstI sites of M13mp9 (Blum, et al., 1989). An additional 150 bp from the middle of the fis gene were deleted by BstEII digestion. M13mp9::Δfis::tet was then transformed into DH5α F' Kan (Gibco-BRL) and the resulting lysate used to produce strain PB755 by homologous recombination. The dps mutant was constructed by transducing strain PBL500 with phage $P_1$ (184593) (zbi-29::Tn10) (Singer, et al., 1989) and $Tet^5$ derivatives were recovered as described in Bochner et al. (1980). Imprecise Tn10 excision deleted dps as indicated by western blot analysis and generation of chlorate resistance (Johnson, et al., 1987).

Definitions

The present invention employs the following definitions:

"Antibody." The term "antibody" is used both to refer to a homogeneous molecular entity, or a mixture such as a serum product made up of a plurality of different molecular entities.

"Chlorine injury." The term "chlorine injury" refers to the sublethal effect of treatment of cells with chlorine (bleach or chloramines) resulting in physiological damage and possible loss of culturability.

"Growing cells" refer to cells which are dividing.

"Growth State" determination refers to measurement that distinguishes between growing and nongrowing cells.

"Growth state-specific protein" refers to protein which is present only in growing cells or only in nongrowing cells and is therefore growth state-specific.

"Non-growing or dormant cells" refers to cells which are not dividing.

"Probe" refers to a specific antibody coupled to a fluorochrome used to measure levels of a specific protein.

"Protein profiling" refers to the determination of the levels of Fis, Dps and DnaK using specific protein probes.

"Unculturable" and "Non-culturable" The term "unculturable" and "non-Culturable" refer to bacteria not capable of forming colonies on a solid medium, or of growing in a liquid medium.

"VNC" refers to bacteria viable but nonculturable.

Method of Use: Use of Growth State-specific Probes to Detect Enterobacteriaceae.

Figure 2:
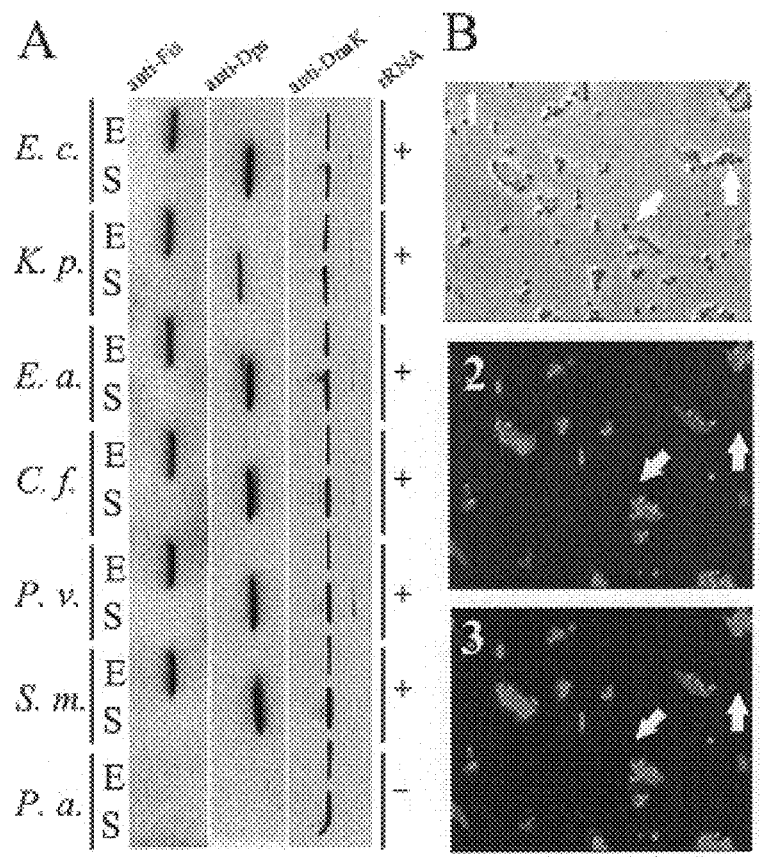
FIG. 2. Phylogenetic Range of Antibody Probes. Western blots of cell extracts of growing (E) and starving (S) wild type Enterobacteiaceae and a gamma subdivision proteobacterium probed with anti-Fis, anti-Dps, or anti-DnaK antibodies visualized by chemiluminescence (A). Single cell detection using an FITC labeled Enterobactetiaceae-specific 16S rRNA probes (+,–). Bright field (B1) and single exposure fluorescent micrographs (B2 and B3) of the same field of cells from raw wastewater probed simultaneously with AMCA labeled anti-DnaK antibody (B2) and an FITC labeled 16S rRNA probe (B3). Representative nonfluorescing cells using either probe are indicated (arrows). Species used were: *E.c., Escherichia coli; K.p., Klebsiella pneumoniae; E.a., Enterobacter aerogenes; C.f., Citrobacter freundii; P.v., Proteus vulgaris; S.m., Serratia marcescens*; and *P.a., Pseudomonas aeruginosa*.

Enterobacteriaceae (coliforms) are a dominant component of municipal wastewater effluent. All of the major genera within this family have been reported in this environment. To verify detection of these genera using the growth state probes, western blots may be performed on selected species. In addition, conservation of target protein regulation can be verified in all cases by testing extracts from growing (E) or nongrowing (S) cells. Dps and Fis are detected under the expected conditions in all members of the Enterobacteriaceae but not other members of the gamma proteobacterial subdivision. (FIG. 2A). A 16S rRNA probe specific for Enterobacteriaceae can be used to detect the enterics but not other gamma proteobacteria. The presence of DnaK in all species tested, indicates that Dps and Fis containing cells are a subset of cells containing DnaK, a critical feature for normalization for subsequent quantitative analysis.

Using oligonucleotides complementary to 16S rRNA as a method for phylogenetic analysis of uncultivated microbes, it can be demonstrated that the growth state probes of the present invention are fully compatible with nucleic acid probes. Untreated wastewater samples may be simultaneously probed with the anti-DnaK-AMCA probe (blue and a Enterobacteriaceae 16S rRNA oligonucleotide-FITC probe (green). Fluorescing cells using either probe exhibit nearly 100% identity. DnaK is present in a wide range of gram negative species.

Method of Use: Determination of Growth State of Bacteria

The protein profiling method of the invention is applicable to all bacteria where the levels of two proteins are measured and where one of these proteins accumulates during growth and is removed during stationary phase and the other protein accumulates during stationary phase and is removed during growth phase. The absolute levels of each and their relative ratio provides a measure of the physiological status of the bacterium. To elucidate growth state, alternative cytosolic proteins may be selected as targets for in situ analysis of cultivated or uncultivated samples. (See Example 9). Samples can be probed simultaneously with antibody probes specific for the protein targets.

Method of Use: Monitoring the Progress of Environmental Remediation Efforts.

The method of the invention can be used in bioremediation processes where the physiological status or activity of the bacteria conducting bioremediation is taken as a measure of toxics removal. The method can be used to monitor this process and provide real-time measurements of process efficiency. The use of endogenous microbes or genetically engineered microbes to remove unwanted pollutants depends on their ability to consume or transform the target chemicals. This can depend on the ability of the microbe to grow sufficiently to create the biomass necessary to have a significant remediation impact. However, in many instances the success of this type of approach is compromised by the inherent toxicity of the target pollutant, of nontarget pollutants or a lack of necessary nutrients. Absence of bacterial proliferation in this environment would preclude successful remediation efforts.

Method of Use: Monitoring of Bacterial Growth State in Industrial Fermentations.

The method of the invention can be applied to reduce the cost and lost time associated with fermentation failures by gaining the ability to diagnose physiological distress in time to modify fermentation conditions and obviate fermentation failure. A key aspect of the use of microbes for the production of materials concerns the ability to cultivate the producing organism at particular growth rates, to particular cell densities or to survive in the stationary phase state. These considerations are necessary in particular instances to permit or prolong product formation, particularly bacterial secondary metabolite products such as antibiotics or protein hydrolases. Traditional methods for assessing growth rate and growth state employ cell counting and oxygen or nutrient consumption as indicators of cell physiological status. While cell counting is useful to assess the status of rapidly dividing populations it is useless for slowly growing or nongrowing cells. Measurements based on oxygen or nutrient consumption are employed extensively but determine a parameter reflecting a population or bulk average and indicate little about individual cells. Oxygen or nutrient consumption therefore have little predictive capacity for emerging physiological changes in cell status because they cannot distinguish small changes in all cells or large changes in subpopulations of cells. When conditions within the fermentation vessel are inappropriate, nonproductive or possibly lethal events ensue leading to fermentation failure and significant cost to the producer.

EXAMPLES

The present invention is further detailed in the following Examples, which are offered by way of illustration and are not intended to limit the invention in any manner. Standard techniques well known in the art or the techniques specifically described below are utilized.

Example 1

Synthesis of Antibody Probes

The fis gene was amplified by PCR using 5'-TTGAATTCATGTTCGAACAACGCG-3' (SEQ ID

NO:1) (F) and 5'-TTCTTAAGAGCATTTAGCTAACC-3' (SEQ ID NO:2) (R) from PBL500. The resulting PCR product was cloned into pUC19 following EcoRI digestion placing fis under $P_{lac}$ control. A DH5α (Gibco-BRL) transformant was used for Fis purification as described in Nash, et al., 1981. Boiling of cell free lysates followed by clarification 200,000×g for 3 h at 4° C. was used prior to ammonium sulfate precipitation to facilitate protein removal. The resulting dialyzed material was fractionated by DNA cellulose chromatography as described for DPS (Almiron, et al., 1992) and purified to homogeneity by electroelution following SDS PAGE.

Preparation of antibodies was as described previously (Blum, et al., 1992; Krska, et al., 1993). Techniques for raising and purifying antibodies are well known in the art and any such techniques may be chosen to achieve the preparations claimed in this invention. Rabbit sera containing anti-DnaK, anti-Dps, and anti-Fis antibodies were processed with acetone powders from homologous mutant strains and then fractionated by immunoaffinity chromatography. The antibodies were further purified by affinity chromatography with protein A-Sepharose as described previously (Krska, et al., 1993). Anti-DnaK antibodies were coupled to 7-amino-4-methylcoumarin-3-acetic acid (AMCA X, SE), anti-Dps antibodies were coupled to fluorescein isothiocyanate (FITC), and anti-Fis antibodies were coupled to TEXAS RED™ X according to manufacturer protocols (Molecular Probes). Other methods of visualizing antibodies known in the art may be used to practice the invention. The 16S rRNA probe specific for Enterobacteriaceae, as described by Mittelman, et al. (1997), having the sequence 5'-CATGAATCACAAAGTGGTAAGCGCC-3' (SEQ ID NO:3), was purchased prelabeled with fluorescein by the manufacturer (Gibco-BRL).

Example 2

Fluorescence Microscopy and Western Blot Analysis

Cells were fixed by resuspending in PBS, adding 4% (w/v) paraformaldehyde, and incubating at 4° C. for three hr with mixing. Washed cells were resuspended in equal parts of PBS and ethanol. Gelatin subbed slides were prepared by dipping clean slides into a solution of 0.1% (w/v) gelatin and 0.01% (w/v) $CrK(SO_4)_2$ in deionized water and then air drying at room temperature for 10 minutes. Fixed cells were applied to treated slides and dried at 37° C. and dehydrated by successive rinses in 50%, 80%, and 98% ethanol. Cell permeabilization was accomplished by lysozyme EDTA treatment (Zarda, et al., 1991) with lysozyme (5 mg/ml) in 100 mM Tris/HCL, 50 mM EDTA (pH 8.0). Rinsed dried slides were then simultaneously treated with all three probes in the dark and suspended in 2% (w/v) BSA, 150 mM NaCl, 100 mM Tris/HCL (pH 7.5) for 1 hr in a humidified chamber. Slides were washed in 150 mM NaCl, 100 mM Tris/HCL (pH 7.5), 1% Triton X-100, 1% Deoxycholic Acid, and 0.1% SDS for 10 min, rinsed in water and dried at 37° C. Fluorochrome bleaching was minimized by phenylenediamine treatment (Wolosewick, 1984) prior to application and sealing of the coverslip. Single cell 16S rRNA analysis using the fluoroscein labeled oligodeoxynucleotide was as described in Giovannoni, et al. (1988). Simultaneous use of antibody and nucleic acid probes employed the standard antibody probe procedure at 42° C. Specificity of the 16S rRNA probe was maintained in the absence of formamide. Fluorescence microscopy of raw and treated waste water bacterial communities were performed in replicate using samples obtained on different days from the wastewater processing facility. Variation in Fis and Dps cellular abundance observed during reconstruction experiments using raw wastewater followed similar trends despite the use of samples obtained on different days.

Fluorescence emission from the fluor-labeled antibody probes was detected using a Microphot epi-fluorescent microscope (Nikon), an LEI-750 CCD camera (Leica) and Omega XF22, XF03 and XF43 filter sets for fluoroscein, AMCA and TEXAS RED™, respectively. Images were captured, cells counted, and fluorescence quantitated using Image-1 image analysis software (Universal Imaging). Fis, Dps and DnaK levels were determined by measuring the fluorescence intensity of their corresponding fluorochrome labeled antibodies; FITC, TEXAS RED™, and AMCA, respectively, for each of 1000 cells per time point. Variation in individual cell permeability was minimized by normalizing Fis and Dps fluorescence to that for DnaK on a per cell basis. Percent of maximum cellular fluorescence was determined by assigning as 100% of the highest level of fluorescence of the normalized Fis/FITC label and the normalized Dps/TEXAS RED™ label. All remaining values were divided by that value and multiplied by 100 to calculate their percent of maximum cellular fluorescence.

Prior to electrophoresis, samples were adjusted to 250 mM Tris-HCL (pH 6.8), 2% SDS, 0.75 M 2-mercaptoethanol, 10% glycerol, 20 µg of bromophenyl blue per ml and boiled for 10 min. Proteins were resolved by SDS-PAGE, with 4% (wt/vol) acrylamide stacking and 16% (wt/vol) acrylamide separating gels as described previously (Rockabrand, et al., 1995; Rockabrand, et al., 1998), with prestained molecular mass markers (Novex). Western blots were prepared essentially as described in Rockabrand, et al. (1998). Western blots were probed with a 1:1,000 dilution of the rabbit sera and then a 1:1,000 dilution of sheep anti-rabbit horseradish peroxidase conjugate (Gibco-BRL). Western blots were processed and developed with the ECL reagent system according to the manufacturer's protocol (Amersham). Chemiluminescence was detected by exposing Kodak XAR film. Protein abundance was determined by comparison to purified standards as described in Rockabrand, et al., (1998).

Example 3

Phylogenetic Specificity of the Protein Profiling Method Using Dps, Fis and DnaK Phylogenetic analysis (distance) of 16S rRNA sequences from selected proteobacteria was performed with PHYLIP 3.57c (Felsenstein, 1989) to examine the generality of the 16S rRNA probe specific for the Enterobacteriaceae (Mittelman, et al., 1997). A 906 nt region spanning positions 496–1502 of the *E. coli* rRNA gene was used to prepare a sequence alignment. Sequence from the following organisms were used to construct the tree; CCRRRNAC (*C. crescentus*), BSUB16SR (*B. subtilis*), D88008 (*A. faecalis*), XO6684 (*P. aeruginosa*), AC16SRD (*A. caleoaceticus*), EA16SRR (*E. amylovra*), M59160 (*S. marcescens*), HAFRR16SA (*H. olvei*), YEN16SA (*Y. enterolitica*), RAATCR (*R. aquatilis*), X07652 (*P. vulgaris*), D78009 (*X. nemotophilus*), KCRRNA16S (*K. cryocrescens*), M59291 (*C. freundii,*), AB004750 (*E. aerogenes*), U33121 (*K. pneumoniae*); AB004754 (*K. oxytoca*), ST16SRD (*S. typhinurium*), SF16SRD (*S. flexneri*), I10328 (*E. coli*). A multiple-sequence alignment was made with CLUSTAL W (Thompson, et al., 1994). SEQBOOT was used to generate 100 bootstrapped data sets. Distance matrices were calculated with DNADIST using the default options. One hundred unrooted trees were inferred by neighbor-joining analysis of the distance matrix data by using NEIGHBOR. Bias introduced by the order of sequence addition was minimized by randomizing the input order. The most frequent branching order was determined with CONSENSE.

Wastewater bacterial communities are comprised of many taxa, although the Enterobacteriaceae or coliforms are of primary importance (Lechevallier, et al., 1980). It was therefore necessary to evaluate the phylogenetic specificity of the antibody probes to discriminate between the percentage of coliform species detectable in wastewater samples relative to the detection frequency of noncoliform species. Western blot analysis of pure cultures of selected species indicated that all major enterobacterial genera contained the target proteins and that their synthesis was regulated as observed in $E.$ $coli$ (FIG. 2A). $P.$ $aeruginosa$ a common wastewater inhabitant (Bahlaoui, et al., 1997) was used as a noncoliform control. A DnaK homolog was detected in this organism (FIG. 2A; Krska, et al., 1993), but Dps and Fis were not evident. These results indicated that the method effectively detected coliforms. To preclude enumeration of noncoliform species, only DnaK containing cells which exhibited detectable levels of either Dps or Fis were scored in subsequent studies.

A 16S rRNA probe specific for the Enterobacteriaceae (Mittelman, et al., 1997) was employed to further test the specificity of the antibody probes using pure cultures (FIG. 2A). The utility of the 16S rRNA probe for detection of a more comprehensive set of Enterobacteriaceae then described previously (Mittelman, et al., 1997), was first verified by phylogenetic analysis and indicated that the probe sequence was complementary to all 16S rRNA sequences of the major genera of the Enterobacteriaceae. Raw wastewater samples analyzed by simultaneously probing with the AMCA-coupled DnaK antibody and fluorescein-coupled 16S rRNA oligonucleotide exhibited nearly complete overlap (99.75%) of cells detected by the two probes (FIG. 2B). These results indicate that noncoliform taxa did not interfere with coliform detection in these studies. These results also demonstrate compatibility between nucleic acid hybridization for taxon identification and protein profiling for physiological analysis.

Example 4

Determining Bacterial Growth State in Chlorinated Wastewater

Wastewater samples were obtained from municipal treatment plants serving a population of 200,000. The wastewater was treated via an activated sludge process followed by disinfection with an injection of chlorine gas which is neutralized before release with sulfur dioxide gas. Initial chlorine concentration in the contact basin was 3.5 mg/L and the contact time was 1 hour. Raw wastewater samples were taken from the effluent of the final or secondary clarifiers prior to chlorination. Chlorinated samples were collected from the effluent from the chlorine contact basin. One liter volumes of secondary treated wastewater were shaken at 200 rpm at 25° C. on a G-33 shaker (New Brunswick). Sodium hypochlorite was added to achieve 3.5 or 7 mg/L available chlorine as indicated. After 1 hr, sodium thiosulfate was added (15 mg/L) to neutralize the remaining free chlorine (Eaton, et al., 1995). Nutrient resupplementation was accomplished by addition of tryptone (0.1% w/v) following neutralization.

The occurrence of chlorine injury of coliforms in chlorinated wastewater was determined as described for drinking water (Bochner t al., 1989; McFeters, et al., 1986; McFeters, et al., 1990). Municipal wastewater chlorination reduced colony forming units (CFU) on selective medium (m-Endo) by nearly 100-fold relative to an untreated sample ($4.92 \times 10^3$ CFU/ml versus $5.02 \times 10^5$ CFU/ml). In contrast, no reduction in plating efficiency was observed using a medium (mT-7) designed to recover chlorine injured coliforms ($5.30 \times 10^5$ CFU/ml). Nearly identical results were obtained from wastewater samples obtained on different days. These results indicate that the loss of culturability observed using selective growth conditions results from the induction of a dormant state by chlorination. To understand the physiological basis for chlorination-induced dormancy in wastewater coliforms, three cytosolic proteins were selected as targets for in situ analysis of uncultivated cells.

Target protein abundance in $E.$ $coli$ populations during growth and starvation initially were determined by Western blot analysis using DnaK, Fis and Dps antibodies (FIG. 1A–C, lanes 1,2). Antibody specificity was verified by the absence of cross reacting material in extracts of mutants lacking the structural genes for the target proteins (FIG. 1A–C, lanes 3,4). Single cell protein profiles then were determined by simultaneously probing a mixed population of growing and starving wild type $E.$ $coli$ with all three antibodies individually coupled to distinct fluorochromes. Examination of individual fields at each of three wavelengths revealed the identity of growing and starving cells (FIG. 1D–F). All cells could be observed using the DnaK probe (FIG. 1D). Starving cells only had high levels of Dps (FIG. 1E) while growing cells only had high levels of Fis (FIG. 1F). Fluorescent antibody probe specificity was confirmed using mixed populations of wild type and mutant $E.$ $coli$ strains for each of the target proteins (FIGS. 1G–L).

Figure 3:
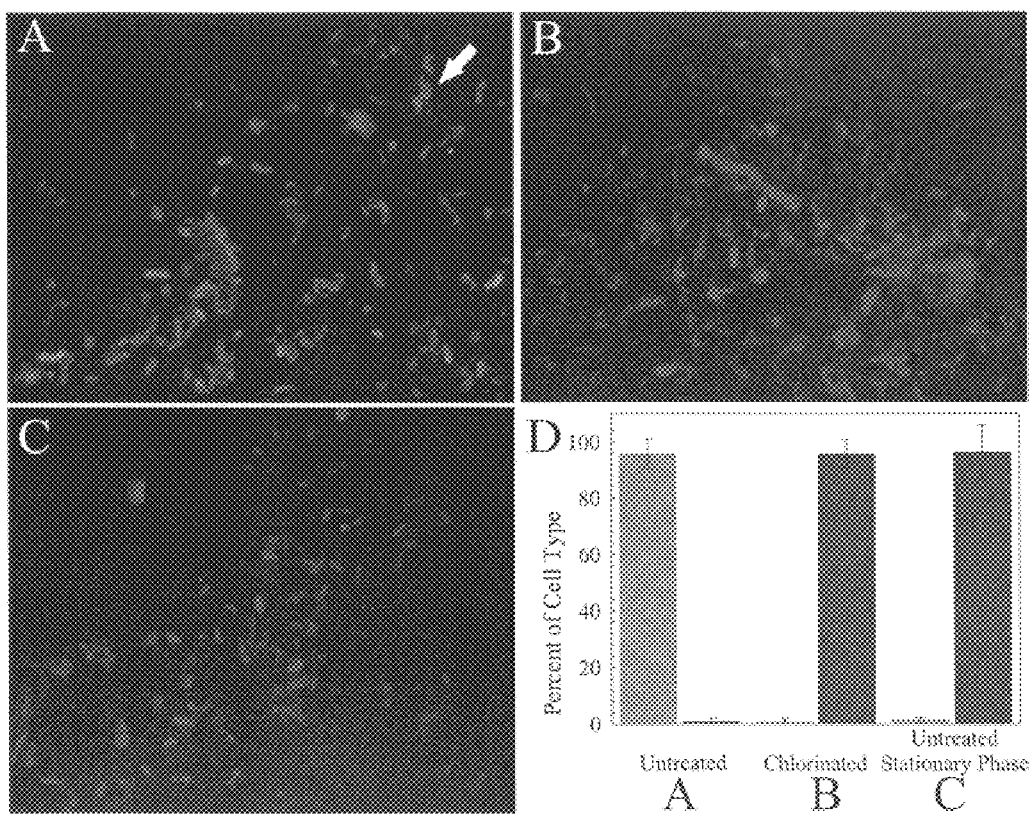
FIG. 3. Growth State and Coliform Bacteria in Chlorinated and Raw Wastewater. Fluorescent micrographs of wastewater samples probed with the three fluor-labeled antibody probes; raw samples (A), raw stationary phase sample (C) and a chlorinated sample (B). Double exposures are shown which combine images of FITC (anti-Fis) and TEXAS RED™ (anti-Dps) probed samples. Quantitation of numbers of cells with detectable Dps or Fis (sometimes referred to herein as FIS) as percentages of total cells examined are shown (D); green bars (Fis containing cells), red bars (Dps containing cells). Error bars indicate the variation observed for each cell type observed between three fields of view, approximately the location of a rare Dps containing cell in untreated wastewater.

The protein profiling procedure was then applied to studies of uncultivated coliforms in chlorinated and raw wastewater. Raw, untreated samples were analyzed using the fluor-labeled antibody probes applied simultaneously. These samples were found to consist primarily of Fis containing cells which were nearly devoid of Dps (FIG. 3A). Only a few cells in such samples contained detectable levels of Dps (FIG. 3A, arrow). The images shown (FIGS. 3A, B and C) are composites of FITC and Texas-Red emission. There was good concordance in this sample between cells found to contain Fis and those containing DnaK. In contrast, chlorinated samples consisted primarily of Dps containing cells with nearly undetectable levels of Fis (FIG. 3B). Again all Dps containing cells also contained DnaK. Surprisingly, cells from raw water samples which had been allowed to enter stationary phase by continued incubation at ambient temperatures also exhibited the high Dps and low Fis protein profile (FIG. 3C). Because of the similarity between chlorinated samples and untreated samples which had been allowed to enter stationary phase, it was unclear whether this protein profile was the result of oxidation or starvation. To understand which stimulus was responsible, wastewater chlorination was tested for its effects on growth of newly inoculated cells. A raw wastewater sample and a chlorinated (neutralized) derivative sample were sterilized by filtration and inoculated with growing wild type $E.$ $coli$. No growth was observed in the treated water after three days of incubation. In the untreated water however, growth (g=3 hr) and a high cell yield ($5.26 \times 10^8$ CFU/mo) was observed. (Table 3). This indicates there were insufficient nutrients to support bacterial growth and therefore that the preponderance of Dps containing cells in chlorinated wastewater result from conditions of starvation.

TABLE 3

| Chlorine addition | Growth rate | Cell yield |
|---|---|---|
| + | NG[a] | ND[b] |
| − | k = 0.33 | 5.26 × 10[8] CFU/ml |

[a]NG = No Growth (72 h)
[b]ND = Not done
Wastewater samples pre and post chlorination were sterile filtered (0.45 μm pore) and 25 mls placed in sterile 125 ml flasks. One ml of NCM533 at 4.9 at 10[5] CFU/ml (determined by plating on LB plates in duplicate) was added to each flask which was then shaken at 200 rpm at room temperature. Growth rate was determined and the cell yield measured after the onset of starvation by plating on LB plates in duplicate.

Figure 4:
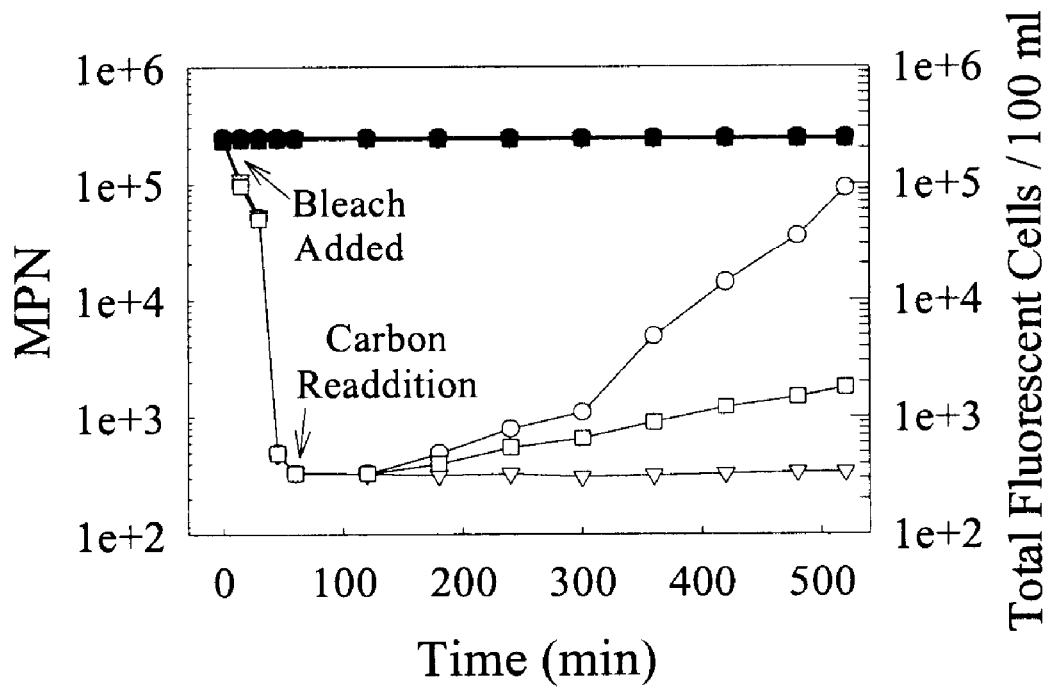
FIG. 4. Coliform Regrowth and Protein Profiling in Chlorinated Wastewater. Most Probable Number (MPN; open symbols) and DnaK containing total fluorescent cell counts (closed symbols) of chlorine treated (3.5 mg/L; ◯, ☐, æ, ▼, or 7 mg/L; ☐, ■) wastewater samples with nutrient supplementation (0.1% w/v tryptone; ◯, æ, ☐, ■) or without additions (∇, ▼) are shown MPN values were determined using EC broth. Total fluorescent (DnaK containing) cell counts were determined using samples with and without nutrient supplementation.

To test the possibility that chlorinated wastewater might be nutrient deficient, raw wastewater samples were chlorinated and then supplemented with nutrients (FIG. 4). Standard chlorination (3.5 mg/L, 1 hr) resulted in an initial 1000-fold reduction in coliform content as determined by Most Probable Number analysis (MPN). Without nutrient supplementation, no subsequent change in MPN values were observed despite prolonged incubation at ambient temperatures (FIG. 4, inverted diamonds). However, in supplemented cultures, culturability reached pretreatment levels within a 9 hr incubation period (FIG. 4, circles). If the increase in culturable fecal coliforms observed after standard chlorine treatment resulted from growth of a small surviving subpopulation, it would necessitate such cells divide with a 54 min doubling time at 24° C. and initiate division without a lag. Since the measured growth rate of endogenous cells in raw water samples was 150 min, rapid regrowth of a subpopulation appears improbable. Instead, the supplementation-induced increase in MPN values more likely results from resuscitation of dormant cells. The rate of increase in MPN values in supplemented cultures was inversely proportional to the degree of chlorination; a doubling of chlorine concentration from 3.5 mg/L to 7.0 mg/L greatly reduced the rate of increase in the appearance of culturable cells (FIG. 4, squares). In this latter case the rate of increase in MPN values was consistent with the regrowth of a subpopulation of surviving cells.

Figure 5:
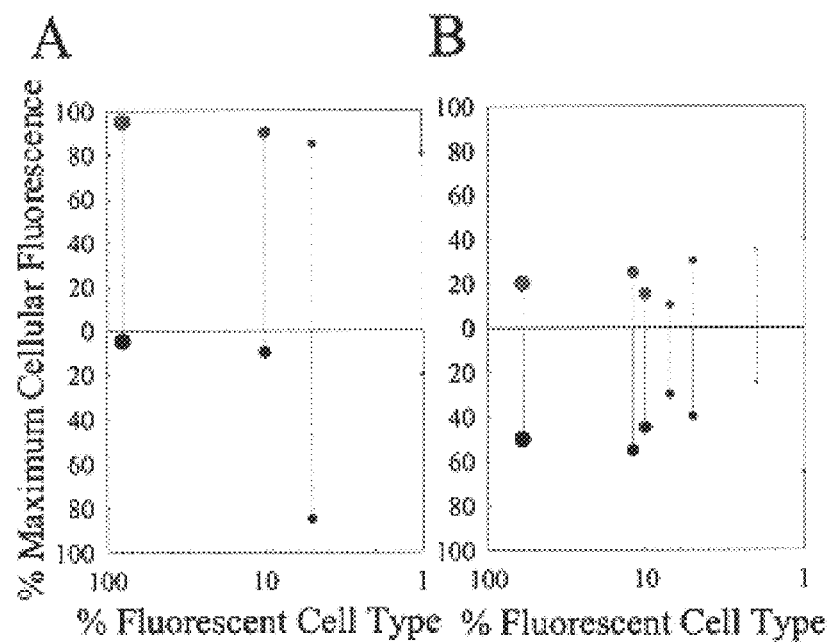
FIG. 5. Quantitative analysis of Fis and Dps cellular content and abundance of cell type following treatment of raw wastewater by chlorination. Samples were examined immediately before (A) or 60 min after (B) treatment. Cellular content of Fis (green balls and lines, upper panel) and Dps (red balls and lines, lower panel) are indicated as percentages of the maximum cellular fluorescence of the brightest cell in each sample (Y-axis). Lines extending from above to below the midpoint line indicate Fis and Dps content respectively of the same individuals. The abundance of cells exhibiting particular degrees of fluorescence are shown as percentages of fluorescent cell type (X-axis). Ball size is proportional to the abundance of that fluorescent cell group using four sizes; large 100–50%, medium 50–10%, small 10–3%, smallest 3%-undetectable. Cells are grouped into clusters based on 5% increments of individual cellular fluorescence.
Figure 6:
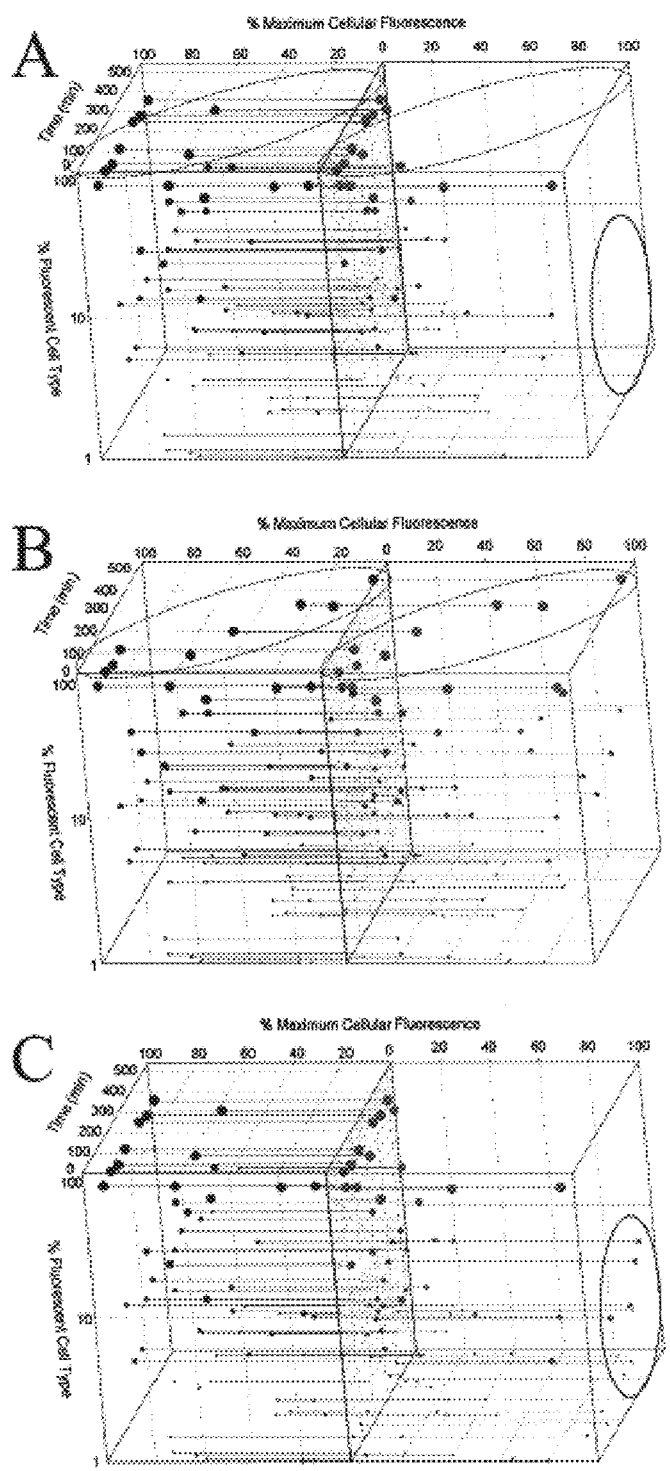
FIG. 6. Quantitative analysis of single cell Fis and Dps content and abundance of cell type. Samples were: chlorine treated (A and B, 3.5 chlorine mg/L; C, 7 mg/L) and either not resupplemented with nutrients (A) or nutrient resupplemented (B, C). The data are presented as indicated in FIG. 5 with the added dimension of experimental time (Z-axis) and the 90° rotation of the figure relative to that shown in the previous figure. Changes in Fis and Dps protein profiles indicating resuscitation (A and B, ovals) and subpopulation regrowth (A and C, circles) are indicated. Similar trends in Fis and Dps cellular concentrations were observed in replicate trials. One thousand cells were examined for each sample time point.

The inability to distinguish between resuscitation of viable but otherwise nonculturable cells rather than regrowth of surviving subpopulations lies at the heart of much recent controversy concerning the VNC state (Barer, 1997; Bogosian, et al., 1998; Dodd, et al., 1997). To resolve this issue in the present case, the fluor-labeled antibody probes were used to quantify the growth state of individual cells by protein profiling in response to chlorination and nutrient supplementation. A raw wastewater sample was chlorinated for 1 hr, neutralized and monitored fr an additional 8 hr. The quantity of Fis (green) and Dps (red) were then examined for 1,000 cells at selected time intervals. The results obtained at the beginning of the experiment and 60 min following chlorination are shown (FIG. 5). The results obtained for the entire experiment are also presented (FIG. 6A). Fis and Dps cellular abundance were determined by normalizing protein-specific fluorescence intensity on an individual cell basis to the amount of DnaK detected in the same cell. This minimized variation resulting from differential cell permeability to the antibody probes. These values are presented as a percentage of the maximum cellular fluorescence observed for all cells. Numbers of cells of specific Fis and Dps content were then summed into groups comprising 5% incremental amounts of either protein and the relative abundance of cells in these groups is shown as a percentage of total fluorescent cells. Upon chlorine addition (FIGS. 5 and 6A) there was a rapid reduction in the number of cells containing Fis and the quantity of Fis in these cells. These changes were largely complete within the treatment time (1 hr) and prior to chlorine neutralization. A concomitant increase in the number of Dps containing cells and the quantity of Dps per cell was also observed. During this period there was no change in the total number of fluorescent (FIG. 4, closed symbols) thus eliminating lysis as a contributing factor.

The response of individual cells to nutrient supplementation following chlorine treatment (3.5 mg/lL) and neutralization was also examined (FIG. 6B). The initial response to chlorination was as observed previously (FIG. 6A). However 2 hr after nutrient addition, an increasing fraction of fluorescent cells changed their protein profile (FIGS. 6A and 6B, ovals). Dps containing cells and the quantity of Dps per cell decreased while Fis containing cells and the quantity of Fis per cell increased. After about 9 hr this change was complete and the protein profile of nearly all cells closely resembled that of cells in raw wastewater. The absence of a significant number of residual Dps containing cells present during this recovery eliminates the hypothesis of subpopulation regrowth by rare surviving cells. Instead the results indicate that chlorination failed to kill coliforms and that the bulk of the cell community were starving and were resuscitated by nutrient supplementation.

Nutrient supplementation of wastewater samples subjected to increased chlorination (7 mg/L, 1 hr) resulted in a much slower increase in culturable fecal coliforms (FIG. 4). To test if this might result from the regrowth of a subpopulation of surviving cells, cell protein profiles were determined (FIG. 6C). A seen previously (FIG. 6B), 2 hr after nutrient supplementation a change became evident in the protein content of a small number of cells in which Fis abundance increased while Dps abundance decreased (FIGS. 6A and 6C, circles). However, the rate of increase of such cells was much slower than observed previously. The abundance of this class of fluorescent cells agreed closely with the MPN values after similar treatment (FIG. 4) and represented only a fraction of a percent of the total fluorescent cells. Such cells may represent rare survivors resulting from the increased level of chlorination which as a result of continued chlorine injury, grow at a reduced rate. This Example 4 is further described in Rockabrand, D., et al., (Manuscript under review), incorporated herein by reference.

Example 5

Monitoring Bacterial Growth State in Industrial Fermentations

The coliform, *Escherichia coli*, is the most frequently used prokaryotic expression system for the production of heterologous proteins, including recombinant antibodies. The ability to diagnose physiological distress of pure cultures of microorganisms so as to modify fermentation conditions can also be accomplished with the method of the invention by assessing protein profiles of healthy or productive cells as a baseline and using this baseline to detect unwanted alterations in protein profiles associated with the "sick" or nonproductive cells. For example, increased levels of Dps protein and decreased levels of Fis protein in cells in a fermentor employing *E. coli* or other coliforms, indicates that growth conditions are no longer optimal and with this information the operator can intercede and attempt to remedy the problem prior to a loss of proliferation of cells and subsequent fermentation run failure. Since the stationary phase state is the growth state employed for production of secondary bacterial metabolites such as most antibiotics, it is of interest to know when cells are not in stationary phase. Protein profiling using the method of the invention detects decreased levels of Dps and elevated levels of Fis indicating that cells are not in the stationary phase and that fermentor conditions (physiological state) is inconsistent with the production of secondary metabolites.

Example 6

Monitoring Bioremediation Efforts

The method of the invention can be applied to single species cultures such as bioremediation processes through the testing of cells obtained from samples to monitor changes in physiological status by protein profiling. The resulting information provides a realtime assessment of the status of the specific species or remediating organism in the artificial environment. If growth is reduced, as indicated, for example, by high Dps levels and low Fis levels, then the operator can consider nutrient addition or dilution to reduce levels of toxic chemicals to re-establish optimal physiological conditions as indicated by changes in protein profiles. As with industrial fermentation, rapid intervention may enable the operator to avoid system failure and therefore costs associated with efforts to restart the remediation all over again.

Example 7

Monitoring Efficiency of Antimicrobial Treatments

The method of the invention can be used to monitor the efficiency of antimicrobial treatments in humans, animals or other assay systems. Successful growth inhibition by the antimicrobial is indicated by, for example, increasing levels of Dps and decreasing levels of Fis. This protein profile information can be used in conjunction with conventional culturability measurements. Bacterial samples obtained from treated hosts can be periodically tested for changes in protein profiles to assess the consequence of antibiotic exposure or the impact of other accompanying treatment regimens such as diet.

Example 8

Alternative Methods of Detecting Levels of Growth State-specific Proteins

Cell sorting using a fluorescence-activated cell sorter (FACS) can be used to quantitate levels of cells with high amounts of alternative growth state-specific proteins, e.g., Dps or Fis. This information provides quantitative measures of cell types and can be used to define population physiological composition and growth status.

Bulk measurements may be equally informative where single cell information is either unnecessary or difficult to obtain due to the use of microscopy equipment. Such methods can employ immunoblot (western blot) procedures, immunoradiometric assays (IRMA), enzyme linked immunosorbant assays (ELISA), or other methods to obtain bulk or average measure of growth state-specific protein levels in target cells.

Example 9

Alternative Growth State-specific Proteins

If the target organism is sufficiently phylogenetically diverse and lacks protein homologs of either Fis, Dps or DnaK, suitable alternatives could be employed to assess growth state status. Examples of protein alternatives to Fis could include other proteins present only during growth such as those which are either unstable and thus must continually be resynthesized to maintain adequate levels such as the ribosomal protein SI. Examples of protein alternatives to Dps include those which are present only in the stationary phase such as the outer membrane protein OmpC. Alternatives to DnaK could include those which are present at all growth states such as the GroEL chaperone. Using these alternative proteins, for example, physiological status would be expressed as the ratio of S1 to OmpC normalized to GrEL, where a large number would indicate cells were growing and a small number would.indicate cells were in stationary phase.

Example 10

Protein Profiling of Gram-positive Bacteria

The gram-positive bacteria i Enterococcus alcolis, has been shown to enter the VNC state under various adverse environmental conditions and to remain viable and capable of resuming active growth (LIeo, et al., 1998). Growth state characteristics can be determined for this species and growth state-specific proteins identified by means known in the art such as 2-D gel electrophoresis or protein subtraction analysis. The proteins can be purified and antibodies raised, purified and analyzed. Specificity can be confirmed by methods known in the art, for example, western blot. These antibodies can be used in the method of the invention to derive a protein profile and thereby distinguish growing from dormant cells.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Almiron, M, et al. (1992). "A novel DNA-binding protein with regulatory and protective roles in starved *Escherichia coli*", *Genes Develop.* 6:2646–2654.

Amann, R. A., et al. (1990). "Fluorescent-oligonucleotide probing of whole cells for determinative, phylogenetic and environmental studies in microbiology", *J. Bacteriol.* 172: 762–770.

Bahlaoui, M. A., et al. (1997). "Dynamics of pollution-indicator and pathogenic bacteria in high-rate oxidation wastewater treatment ponds", *Water Res.* 31:630–638.

Ball, C. A., et al. (1992). "Dramatic changes in Fis levels upon nutrient upshift in *Escherichia coli*", *J. Bacteriol* 174:8043–8056.

Ballentine, R. K., et al. (1986). "Ambient water quality criteria for bacteria", *Environmental Protection Agency.* 440/5-84-001.

Barer, M. R. (1997). "Viable but non-culturable and dormant bacteria: time to resolve an oxymoron and a misnomer", *J. Med. Microbiol.* 46:629–631.

Barns, S. M., et al. (1994). "Remarkable archaeal diversity detected in a yellowstone national park hot spring environment", *Proc. Natl. Acad. Sci. U.S.A.*, 91:1609–1613.

Blum, P. H. (1997). "Molecular genetics of the bacterial stationary phase," pp. 351–367, in *Bacteria in the Olig-* otrophic Environment, with Special Emphasis on Starvation Survival, R. Morita, Ed. (Chapman and Hall, New York, N.Y.).

Blum, P., et al. (1992). "Physiological consequences of DnaK and DnaJ overproduction in Escherichia coli", J. Bacteriol. 174:7436–7444.

Blum, P., et al. (1989). "Gene replacement and retrieval with recombinant M13mp bacteriophages", J. Bacteriol. 171:538–546.

Bochner, B. R., et al. (1980). "Positive selection for loss of tetracycline resistance", J. Bacteriol. 143:926–933.

Bogosian, G., et al. (1998). "A mixed culture recovery method indicates that enteric bacteria do not enter the viable but nonculturable state", Appl. Environ. Microbiol., 64:1736–1742.

Bukau, B., et al. (1989). "Deletion ΔdnaK52 mutants of Escherichia coli have defects in chromosome segregation and plasmid maintenance at normal growth temperatures", J. Bacteriol 171:6030–6038.

Camper, A. K., et al. (1979). "Chlorine injury and the enumeration of waterborne coliform bacteria", Appl. Environ. Microbiol. 37:633–641.

Colwell, R. R. (1996). "Global climate and infectious disease: the cholera paradigm", Science 274:2025–2031.

Dawes, L. L., et al. (1978). "Bactericidal property of seawater: death or debilitation", Appl. Environ. Microbiol. 35:829–833.

Dodd, C. E., et al. (1997). "Inimical processes: bacterial self-destruction and sub-lethal injury", Trends Food Sci. Technol. 8:238–241.

Eaton, A. D., et al. (1995). Standard Methods for the Examination of Water and Wastewater, 19th Ed. (American Public Health Assoc., Washington, D.C.)

Felsenstein, J. (1989). "PHYLIP-phylogeny interface", version 3.2, Cladistics 5:164–166.

Giovannoni, S. J., et al. (1988). "Phylogenetic group-specific oligodeoxynucleotide probes for identification of single microbial cells", J. Bacteriol. 170:720–726.

Georgopoulos, C. (1992). "The emergence of the chaperone machines", Trends Bioch. Genet. 17:295–299.

Goodrich-Blair, H., et al. (1996). "Regulation of gene expression in stationary phase", In: Regulation of gene expression in Escherichia coli, pp. 571–583; E. C. C. Lin and A. Simon Lynch, Eds. (Chapman and Hall), Hengge-Aronis, R. (1996). "Stationary-phase gene regulation", In Escherichia coli and Salmonella cellular and molecular biology, pp. 1497–1512; F. C. Neidhardt, et al., Eds. (ASM Press).

Johnson, R. C., et al. (1988). "Isolation of the gene encoding the hin recombinational enhancer binding protein", Proc. Natl. Acad. Sci. 85:3484–3488.

Johnson, M. E., et al. (1987). "Involvement of chlA, E M, and N loci in Escherichia coli molybdopterin biosynthesis", J. Bacteriol. 169:117–125.

Koch, C., et al. (1988). "Escherichia coli host factor for site-specific DNA inversion: cloning and characterization of the fis gene", Proc. Natl. Acad. Sci. 85:4237–4241.

Kohara, Y. (1987). "The physical map of the whole E. coli chromosome: application of a new strategy for rapid analysis and sorting of a large genomic library", Cell 50:495–508.

Krska, J., et al. (1993). "Monoclonal antibody recognition and function of a DnaK (HSP70) epitope found in gram-negative bacteria", J. Bacteriol. 175:6433–6440.

Lechevallier, M., et al. (1980). "Enumeration and characterization of standard plate count bacteria in chlorinated and raw water supplies", Appl. Environ. Microbiol. 40:922–930.

Lomovskaya, O. L., et al. (1994). "Characterization of the $\sigma^{38}$-dependent expression of a core Escherichia coli starvation gene, pexB", J. Bacteriol. 176:3928–3935.

Mayhew, M., et al. (1996). "Molecular chaperone proteins", In: Escherichia coli and Salmonella cellular and molecular biology, pp. 922–937; F. C. Neidhardt, et al., Eds. (ASM Press).

McFeters, G. A., et al. (1986). "Injured coliforms in drinking water", Appl. Environ. Microbiol. 51:1–5.

McFeters, G. A. (1990). "Enumeration occurrence and significance of injured indicator bacteria in drinking water", In: Drinking water microbiology, Chap. 23, pp. 478–492; G. McFeters, Ed. (Springer Verlag, New York, N.Y.).

Miller, J. H. (1972). Experiments in Molecular Genetics (Cold Spring Harbor Press, Cold Spring Harbor, N.Y.).

Mittelman, M. W., et al. (1997). "Rapid detection of Enterobacteriaceae in urine by fluorescent 16S rRNA in situ hybridization on membrane filters", J. Microbiol. Methods 30:153–160.

Morita, R. Y. (1997). Bacteria in Oligotrophic Environments (Chapman Hall, New York, N.Y.).

Nash, H. A., et al. (1981). "Purification and properties of the Escherichia coli protein factor required for A integrative recombination", J. Biol. Chem., 256:9246–9253.

National Technical Advisory Committee (1968). "Water quality criteria", Federal Water Pollution Control Administration.

Nilsson, L., et al. (1992). "Fis-dependent trans activation of stable RNA operons of Escherichia coli under various growth conditions", J. Bacteriol. 174: 921–929.

Notley, L., et al. (1996). "Induction of RpoS-dependent functions in glucose-limited continuous culture: what level of nutrient limitation induces the stationary phase of Escherichia coli?" J. Bacteriol. 178:1465–1468.

Oliver, J. D. (1993). "Formation of viable but nonculturable cells", pp. 239–272, In: Starvation in Bacteria, S. Keleberg, Ed. (Plenum Press, New York, N.Y.).

Partridge, J., et al. (1993). "Cloning, molecular analysis and expression of the Erysipelothrix rhusiopathiae dnaK gene", Infection and Immunity 61:411–417.

Postgate, J. R., et al. (1962). "The survival of starved bacteria", J. Gen. Microbiol. 26:1–18.

Ravel, L., et al. (1995). "Temperature-induced recovery of Vibrio cholera from the viable but nonculturable state: growth or resuscitation?" Microbiol. 141:377–383.

Rockabrand, D., et al. (1995). "An essential role for the Escherichia coli DnaK protein in starvation-induced thermotolerance, $H_2O_2$ resistance and reductive division", J. Bacteriol. 177:3695–3703.

Rockabrand, D., et al. (1995). "Multicopy plasmid suppression of stationary phase chaperone toxicity in Escherichia coli by phosphogluconate dehydratase and the N-terminus of DnaK", Mol. Gen. Genet. 249:498–506.

Rockabrand, D., et al. (1998). "Roles of DnaK and RpoS in starvation-induced thermotolerance of Escherichia coli", J. Bacteriol. 180:846–854.

Rockabrand, D., et al. (Manuscript under Review). "Bacterial Growth and Dormancy Distinguished by Single Cell Protein Profiling: Does Chlorination Kill Coliforms in Municipal Effluent?" Appl. Environ. Microbiol.

Singer, M., et al. (1989). "A collection of strains containing genetically linked alternating antibiotic resistance elements for genetic mapping of Escherichia coil", Microbiol. Rev. 53:1–24.

Spence, J., et al. (1990). "Role of *Escherichia coli* heat shock protein DnaK and HtpG (C62.5) in response to nutritional deprivation", *J. Bacteriol.* 172:7157–7166.

Staley, J. T., et al. (1985). "Measurement of in situ activities of nonphotosynthetic microorganisms in aquatic and terrestrial habitats", *Annu. Rev. Microbiol.*, 39:1379–1384.

Xu, J. S., et al. (1982). "Survival and viability of nonculturable *Escherichia coli* and *Vibrio cholerae* in the estuarine and marine environment", *Mcrob. Ecol.* 8:313–323.

Zarda, B. (1991). "Identification of single bacterial cells using digoxigenin-labeled rRNA-targeted oligonucleotides", *J. Gen. Microbiol.* 137:2823–2830.

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
ttgaattcat gttcgaacaa cgcg                                              24

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
ttcttaagag catttagcta acc                                               23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 3
catgaatcac aaagtggtaa gcgcc                                             25
```

Thompson, J. D., et al. (1994). "CLUSTAL W: improving the sensitivity of progressive multiple sequence alignment through sequence weighting, positions-specific gap penalties and weight matrix choice", *Nucl. Acids Res.* 22:4673–4680.

U.S. Environmental Protection Agency (1995). "National pollutant discharge elimination system permit application requirements for publicly owned treatment works and other treatment works treating domestic sewage", *Fed. Regist.* 60:62562–62569.

Thompson, J. F., et al. (1987). "Cellular factors couple recombination with growth phase: characterization of a new component in the A site-specific recombination pathway", *Cell* 50:901–908.

Whitesides, M. D., et al. (1997). "Resuscitation of *Vibrio vulnificus* from the viable but nonculturable state", *Appl. Environ. Microbiol.* 60:3284–3291.

Wolosewick, J. J. (1984). "Cell fine structure and protein antigenicity after polyethylene glycol processing, in: The science of biological specimen preparation", pp. 83–95; J. P. Revel, et al., Eds. (SEM Inc., AMF O'Hare, Ill.).

What is claimed is:

1. A method for assessing the physiological status of individual cells of enterobacteria in wastewater or drinking water, comprising:
   (a) obtaining a sample comprising enterobacteria from the wastewater or drinking water;
   (b) identifying at least two proteins produced by said enterobacteria, wherein at least one of said proteins (first protein) accumulates during growth phase, and decreases during stationary phase and wherein one of said proteins (second protein) accumulates during stationary phase and decreases during growth phase;
   (c) contacting the enterobacteria in said sample with a labeled antibody probe to said first protein and with a different labeled antibody probe to said second protein;
   (d) detecting said first and said second labeled antibody probes associated with the individual cells of enterobacteria in the sample;
   wherein:
      (i) individual cells of enterobacteria with a detectable level of the antibody probe to said first protein and an undetectable level of the antibody probe to said second protein are in exponential phase;

(ii) individual cells of enterobacteria with an undetectable level of the antibody probe to said first protein and a detectable level of the antibody probe to said second protein are in stationary phase; and (iii) individual cells of enterobacteria with a detectable level of the antibody probes to both of said first protein and said second protein indicates enterobacteria in transition between exponential phase and stationary phase or vice versa.

2. The method of claim 1, wherein said enterobacteria is *Escherichia coli*.

3. The method of claim 1, wherein said first protein is Fis and said second protein is Dps.

4. The method of claim 3, wherein said antibodies are selected from the group consisting of anti-Dps and anti-Fis.

5. The method of claim 1, wherein at least one of the labels is a fluorochrome and said detection of labeled antibody probes is by fluorescence emission.

6. The method of claim 5, wherein said fluorochrome is selected from the group consisting of fluorescein isothiocyanate, a sulfonyl chloride derivative of Sulforhodamine 101, and 7-Amino-4-methylcoumarin-3-acetic acid.

7. The method of claim 5, wherein said detection by fluorescence emission comprises a method selected from the group consisting of fluorescence microscopy, western blot, immunoradiometric assay, fluorescence-activated cell sorting and enzyme linked immunosorbant assays.

8. The method of claim 7, wherein said detection method is fluorescence microscopy.

9. The method of claim 8, wherein said first protein is Fis and said second protein is Dps.

10. A method for assessing the physiological status of individual cells of enterobacteria in a microbial-based hazardous waste treatment process, comprising:

(a) obtaining a sample comprising enterobacteria from the treatment process;

(b) identifying at least two proteins produced by said enterobacteria, wherein at least one of said proteins (first protein) accumulates during growth phase, and decreases during stationery phase and wherein one of said proteins (second protein) accumulates during stationery phase and decreases during growth phase;

(c) contacting the enterobacteria in said sample of enterobacteria with a labeled antibody probe to said first protein and with a different labeled antibody probe to said second protein;

(d) detecting said first and said second labeled antibody probes associated with said individual cells of enterobacteria in the sample; and wherein:

(i) individual cells of enterobacteria with a detectable level of the antibody probe to said first protein and an undetectable level of the antibody probe to said second protein are in exponential phase;

(ii) individual cells of enterobacteria with an undetectable level of the antibody probe to said first protein and a detectable level of the antibody probe to said second protein are in stationary phase; and (iii) individual cells of enterobacteria with a detectable level of the antibody probes to both of said first protein and said second protein indicates enterobacteria in transition between exponential phase and stationary phase or vice versa.

11. The method of claim 10, wherein said first protein is Fis and said second protein is Dps.

12. A method for assessing the physiological status of individual cells of enterobacteria utilized in an industrial fermentation process, comprising:

(a) obtaining a sample comprising enterobacteria from the fermentation process;

(b) identifying at least twos proteins produced by said bacteria, wherein at least one of said proteins (first protein) accumulates during growth phase, and decreases during stationery phase and wherein one of said proteins (second protein) accumulates during stationery phase and decreases during growth phase;

(c) contacting the enterobacteria in said sample with a labeled antibody probe to said first protein and with a different labeled antibody probe to said second protein;

(d) detecting said first and said second labeled antibody probes associated with the individual cells of enterobacteria in the sample; and wherein:

(i) individual cells of enterobacteria with a detectable level of the antibody probe to said first protein and an undetectable level of the antibody probe to said second protein are in exponential phase;

(ii) individual cells of enterobacteria with an undetectable level of the antibody probe to said first protein and a detectable level of the antibody probe to said second protein are in stationary phase; and (iii) individual cells of enterobacteria with a detectable level of the antibody probes to both of said first protein and said second protein indicates enterobacteria in transition between exponential phase and stationary phase or vice versa.

13. The method of claim 12, wherein said first protein is Fis and said second protein is Dps.

14. A method for assessing the physiological status of individual cells of enterobacteria utilized in an antimicrobial treatment process, comprising:

(a) obtaining a sample, comprising enterobacteria from the antimicrobial,treatment process;

(b) identifying at least two proteins produced by said enterobacteria, wherein at least one of said proteins (first protein) accumulates during growth phase, and decreases during stationery phase and wherein one of said proteins (second protein) accumulates during stationery phase and decreases during growth phase;

(c) contacting the enterobacteria in said sample with a labeled antibody probe to said first protein and with a different labeled antibody probe to said second protein;

(d) detecting said first and said second labeled antibody probes associated with individual cells of enterobacteria in said sample;

(e) determining a level of each labeled probe associated with the individual enterobacteria;

wherein:

(i) individual cells of enterobacteria with a detectable level of the antibody probe to said first protein and an undetectable level of the antibody probe to said second protein are in exponential phase;

(ii) individual cells of enterobacteria with an undetectable level of the antibody probe to said first protein and a detectable level of the antibody probe to said second protein are in stationary phase; and (iii) individual cells of enterobacteria with a detectable level of the antibody probes to both of said first protein and said second protein indicates enterobacteria in transition between exponential phase and stationary phase or vice versa.

15. The method of claim 14, wherein said first protein is Fis and said second protein is Dps.

* * * * *

UNITED STATES PATENT AND TRADEMARK OFFICE
CERTIFICATE OF CORRECTION

| | | |
|---|---|---|
| PATENT NO. | : 6,569,635 B1 | Page 1 of 1 |
| APPLICATION NO. | : 09/313277 | |
| DATED | : May 27, 2003 | |
| INVENTOR(S) | : Paul Blum | |

It is certified that error appears in the above-identified patent and that said Letters Patent is hereby corrected as shown below:

In column 1 after the paragraph referencing the related applications in the Specification, please insert the following statement which should read
--Statement Regarding Federally Sponsored Research and Funding: This invention was made with U.S. Government support under Grant No. MCB9604000 awarded by the National Science Foundation. The government has certain rights in this invention.--

Signed and Sealed this

Twenty-sixth Day of February, 2008

JON W. DUDAS
*Director of the United States Patent and Trademark Office*